US009675679B2

(12) United States Patent
Zorrilla et al.

(10) Patent No.: US 9,675,679 B2
(45) Date of Patent: Jun. 13, 2017

(54) VACCINES AND METHODS FOR CONTROLLING ADIPOSITY

(75) Inventors: Eric P. Zorrilla, San Diego, CA (US); Michael M. Meijler, Omer (IL); Kim D. Janda, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 1128 days.

(21) Appl. No.: 12/374,908

(22) PCT Filed: Aug. 1, 2007

(86) PCT No.: PCT/US2007/074976
§ 371 (c)(1), (2), (4) Date: Jan. 23, 2009

(87) PCT Pub. No.: WO2008/016976
PCT Pub. Date: Feb. 7, 2008

(65) Prior Publication Data

US 2010/0021487 A1 Jan. 28, 2010

Related U.S. Application Data

(60) Provisional application No. 60/821,071, filed on Aug. 1, 2006.

(51) Int. Cl.
*A61K 39/385* (2006.01)
*A61P 3/00* (2006.01)
*A61K 39/00* (2006.01)
*C07K 14/60* (2006.01)

(52) U.S. Cl.
CPC .......... *A61K 39/0005* (2013.01); *C07K 14/60* (2013.01); *A61K 2039/6081* (2013.01); *C07K 2319/31* (2013.01)

(58) Field of Classification Search
CPC .... A61K 2300/00; A61K 38/00; A61K 38/25; A61K 38/27; C07K 14/60
See application file for complete search history.

(56) References Cited

U.S. PATENT DOCUMENTS

| | | | | |
|---|---|---|---|---|
| 6,967,237 | B2 * | 11/2005 | Bednarek | 530/300 |
| 2003/0113819 | A1 * | 6/2003 | Horton et al. | 435/7.23 |
| 2004/0076645 | A1 * | 4/2004 | Bachmann et al. | 424/204.1 |
| 2007/0237775 | A1 * | 10/2007 | Kikly et al. | 424/141.1 |

OTHER PUBLICATIONS

Campbell (Monoclonal Antibody Technology, 1984, Chapter 1, pp. 1-32).*

* cited by examiner

*Primary Examiner* — Sharon Wen
(74) *Attorney, Agent, or Firm* — Hugh Wang; Thomas Fitting

(57) ABSTRACT

The invention features immunoconjugates for impeding weight gain and treating obesity in a subject. The immunoconjugates comprise particular ghrelin polypeptides and a suitable carrier moiety.

9 Claims, 3 Drawing Sheets

* denotes site of conjugation with KLH or BSA

Ghr1

Ghr2

Ghr3

SEQUENCE LISTING

```
<160> NUMBER OF SEQ ID NOS: 34

<210> SEQ ID NO 1
<211> LENGTH: 5
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of
      formula (I).

<400> SEQUENCE: 1

Gly Ser Xaa Phe Leu
1               5


<210> SEQ ID NO 2
<211> LENGTH: 23
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (6)..(6)
<223> OTHER INFORMATION: Xaa at position 6 is either Lys (K) or Arg (R).
<220> FEATURE:
<221> NAME/KEY: MISC_FEATURE
<222> LOCATION: (7)..(7)
<223> OTHER INFORMATION: Xaa at position 7 is either Ala (A) or Val (V).

<400> SEQUENCE: 2

Ser Pro Glu His Gln Xaa Xaa Gln Gln Arg Lys Glu Ser Lys Lys Pro
1               5                   10                  15

Pro Ala Lys Leu Gln Pro Arg
            20


<210> SEQ ID NO 3
<211> LENGTH: 6
<212> TYPE: PRT
<213> ORGANISM: Artificial
<220> FEATURE:
```

```
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of
      formula (I).

<400> SEQUENCE: 3

Gly Ser Xaa Phe Leu Ser
1               5


<210> SEQ ID NO 4
<211> LENGTH: 7
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of
      formula (I).

<400> SEQUENCE: 4

Gly Ser Xaa Phe Leu Ser Pro
1               5


<210> SEQ ID NO 5
<211> LENGTH: 8
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of
      formula (I).

<400> SEQUENCE: 5

Gly Ser Xaa Phe Leu Ser Pro Glu
1               5


<210> SEQ ID NO 6
<211> LENGTH: 9
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of
      formula (I).

<400> SEQUENCE: 6

Gly Ser Xaa Phe Leu Ser Pro Glu His
1               5


<210> SEQ ID NO 7
<211> LENGTH: 10
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of
      formula (I).
```

-continued

<400> SEQUENCE: 7

Gly Ser Xaa Phe Leu Ser Pro Glu His Gln
1 5 10

<210> SEQ ID NO 8
<211> LENGTH: 11
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of formula (I).
<220> FEATURE:
<221> NAME/KEY: MISC_FEATURE
<222> LOCATION: (11)..(11)
<223> OTHER INFORMATION: Xaa at position 11 is either Lys (K) or Arg (R).

<400> SEQUENCE: 8

Gly Ser Xaa Phe Leu Ser Pro Glu His Gln Xaa
1 5 10

<210> SEQ ID NO 9
<211> LENGTH: 12
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE,
<222> LOCATION: (3)..(3)
<223> OTHER INFORMATION: Xaa at position 3 is a modified serine of formula (I).
<220> FEATURE:
<221> NAME/KEY: MISC_FEATURE
<222> LOCATION: (11)..(11)
<223> OTHER INFORMATION: Xaa at position 11 is either Lys (K) or Arg (R).
<220> FEATURE:
<221> NAME/KEY: MISC_FEATURE
<222> LOCATION: (12)..(12)
<223> OTHER INFORMATION: Xaa at position 11 is either Ala (A) or Val (V).

<400> SEQUENCE: 9

Gly Ser Xaa Phe Leu Ser Pro Glu His Gln Xaa Xaa
1 5 10

<210> SEQ ID NO 10
<211> LENGTH: 13
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of formula (I).
<220> FEATURE:
<221> NAME/KEY: MISC_FEATURE
<222> LOCATION: (11)..(11)
<223> OTHER INFORMATION: Xaa at position 11 is either Lys (K) or Arg (R).
<220> FEATURE:
<221> NAME/KEY: MISC_FEATURE
<222> LOCATION: (12)..(12)
<223> OTHER INFORMATION: Xaa at position 12 is either Ala (A) or Val (V).

-continued

<400> SEQUENCE: 10

Gly Ser Xaa Phe Leu Ser Pro Glu His Gln Xaa Xaa Gln
1               5                   10

<210> SEQ ID NO 11
<211> LENGTH: 14
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of formula (I).
<220> FEATURE:
<221> NAME/KEY: MISC_FEATURE
<222> LOCATION: (11)..(11)
<223> OTHER INFORMATION: Xaa at position 11 is either Lys (K) or Arg (R).
<220> FEATURE:
<221> NAME/KEY: MISC_FEATURE
<222> LOCATION: (12)..(12)
<223> OTHER INFORMATION: Xaa at position 12 is either Ala (A) or Val (V).

<400> SEQUENCE: 11

Gly Ser Xaa Phe Leu Ser Pro Glu His Gln Xaa Xaa Gln Gln
1               5                   10

<210> SEQ ID NO 12
<211> LENGTH: 15
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of formula (I).
<220> FEATURE:
<221> NAME/KEY: MISC_FEATURE
<222> LOCATION: (11)..(11)
<223> OTHER INFORMATION: Xaa at position 11 is either Lys (K) or Arg (R).
<220> FEATURE:
<221> NAME/KEY: MISC_FEATURE
<222> LOCATION: (12)..(12)
<223> OTHER INFORMATION: Xaa at position 12 is either Ala (A) or Val (V).

<400> SEQUENCE: 12

Gly Ser Xaa Phe Leu Ser Pro Glu His Gln Xaa Xaa Gln Gln Arg
1               5                   10                  15

<210> SEQ ID NO 13
<211> LENGTH: 16
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of formula (I).
<220> FEATURE:
<221> NAME/KEY: MISC_FEATURE
<222> LOCATION: (11)..(11)
<223> OTHER INFORMATION: Xaa at position 11 is either Lys (K) or Arg (R).
<220> FEATURE:

<221> NAME/KEY: MISC_FEATURE
<222> LOCATION: (12)..(12)
<223> OTHER INFORMATION: Xaa at position 12 is either Ala (A) or Val (V).

<400> SEQUENCE: 13

Gly Ser Xaa Phe Leu Ser Pro Glu His Gln Xaa Xaa Gln Gln Arg Lys
1 5 10 15

<210> SEQ ID NO 14
<211> LENGTH: 17
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of formula (I).
<220> FEATURE:
<221> NAME/KEY: MISC_FEATURE
<222> LOCATION: (11)..(11)
<223> OTHER INFORMATION: Xaa at position 11 is selected from Lys (K) or Arg (R).
<220> FEATURE:
<221> NAME/KEY: MISC_FEATURE
<222> LOCATION: (12)..(12)
<223> OTHER INFORMATION: Xaa at position 12 is selected from Ala (A) or Val (V).

<400> SEQUENCE: 14

Gly Ser Xaa Phe Leu Ser Pro Glu His Gln Xaa Xaa Gln Gln Arg Lys
1 5 10 15

Glu

<210> SEQ ID NO 15
<211> LENGTH: 18
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of formula (I).
<220> FEATURE:
<221> NAME/KEY: MISC_FEATURE
<222> LOCATION: (11)..(11)
<223> OTHER INFORMATION: Xaa at position 11 is either Lys (K) or Arg (R).
<220> FEATURE:
<221> NAME/KEY: MISC_FEATURE
<222> LOCATION: (12)..(12)
<223> OTHER INFORMATION: Xaa at position 12 is either Ala (A) or Val (V).

<400> SEQUENCE: 15

Gly Ser Xaa Phe Leu Ser Pro Glu His Gln Xaa Xaa Gln Gln Arg Lys
1 5 10 15

Glu Ser

<210> SEQ ID NO 16
<211> LENGTH: 19
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE

```
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or Arg
      (R).
<220> FEATURE:
<221> NAME/KEY: MISC_FEATURE
<222> LOCATION: (12)..(12)
<223> OTHER INFORMATION: Xaa at position 12 is either Ala (A) or Val
      (V).

<400> SEQUENCE: 16

Gly Ser Xaa Phe Leu Ser Pro Glu His Gln Xaa Xaa Gln Gln Arg Lys
1               5                   10                  15

Glu Ser Lys


<210> SEQ ID NO 17
<211> LENGTH: 20
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or Arg
      (R).
<220> FEATURE:
<221> NAME/KEY: MISC_FEATURE
<222> LOCATION: (12)..(12)
<223> OTHER INFORMATION: Xaa at position 12 is either Ala (A) or Val
      (V).

<400> SEQUENCE: 17

Gly Ser Xaa Phe Leu Ser Pro Glu His Gln Xaa Xaa Gln Gln Arg Lys
1               5                   10                  15

Glu Ser Lys Lys
            20


<210> SEQ ID NO 18
<211> LENGTH: 21
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or Arg
      (R).
<220> FEATURE:
<221> NAME/KEY: MISC_FEATURE
<222> LOCATION: (12)..(12)
<223> OTHER INFORMATION: Xaa at position 12 is either Ala (A) or Val
      (V).

<400> SEQUENCE: 18

Gly Ser Xaa Phe Leu Ser Pro Glu His Gln Xaa Xaa Gln Gln Arg Lys
1               5                   10                  15
```

```
Glu Ser Lys Lys Pro
            20


<210> SEQ ID NO 19
<211> LENGTH: 22
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or Arg
      (R).
<220> FEATURE:
<221> NAME/KEY: MISC_FEATURE
<222> LOCATION: (12)..(12)
<223> OTHER INFORMATION: Xaa at position 12 is either Ala (A) or Val
      (V).

<400> SEQUENCE: 19

Gly Ser Xaa Phe Leu Ser Pro Glu His Gln Xaa Xaa Gln Gln Arg Lys
1               5                   10                  15

Glu Ser Lys Lys Pro Pro
            20


<210> SEQ ID NO 20
<211> LENGTH: 23
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or Arg
      (R).
<220> FEATURE:
<221> NAME/KEY: MISC_FEATURE
<222> LOCATION: (12)..(12)
<223> OTHER INFORMATION: Xaa at position 12 is either Ala (A) or Val
      (V).

<400> SEQUENCE: 20

Gly Ser Xaa Phe Leu Ser Pro Glu His Gln Xaa Xaa Gln Gln Arg Lys
1               5                   10                  15

Glu Ser Lys Lys Pro Pro Ala
            20


<210> SEQ ID NO 21
<211> LENGTH: 24
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
```

```
<221> NAME/KEY: MISC_FEATURE
<222> LOCATION: (11)..(11)
<223> OTHER INFORMATION: Xaa at position 11 is either Lys (K) or Arg
      (R).
<220> FEATURE:
<221> NAME/KEY: MISC_FEATURE
<222> LOCATION: (12)..(12)
<223> OTHER INFORMATION: Xaa at position 12 is either Ala (A) or Val
      (V).

<400> SEQUENCE: 21

Gly Ser Xaa Phe Leu Ser Pro Glu His Gln Xaa Xaa Gln Gln Arg Lys
1               5                   10                  15

Glu Ser Lys Lys Pro Pro Ala Lys
            20


<210> SEQ ID NO 22
<211> LENGTH: 25
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or Arg
      (R).
<220> FEATURE:
<221> NAME/KEY: MISC_FEATURE
<222> LOCATION: (12)..(12)
<223> OTHER INFORMATION: Xaa at position 12 is either Ala (A) or Val
      (V).

<400> SEQUENCE: 22

Gly Ser Xaa Phe Leu Ser Pro Glu His Gln Xaa Xaa Gln Gln Arg Lys
1               5                   10                  15

Glu Ser Lys Lys Pro Pro Ala Lys Leu
            20                  25


<210> SEQ ID NO 23
<211> LENGTH: 26
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of
      formula (I).
<220> FEATURE:
<221> NAME/KEY: MISC_FEATURE
<222> LOCATION: (11)..(11)
<223> OTHER INFORMATION: Xaa at position 11 is either Lys (K) or Arg
      (R).
<220> FEATURE:
<221> NAME/KEY: MISC_FEATURE
<222> LOCATION: (12)..(12)
<223> OTHER INFORMATION: Xaa at position 12 is either Ala (A) or Val
      (V).

<400> SEQUENCE: 23

Gly Ser Xaa Phe Leu Ser Pro Glu His Gln Xaa Xaa Gln Gln Arg Lys
1               5                   10                  15

Glu Ser Lys Lys Pro Pro Ala Lys Leu Gln
            20                  25
```

<210> SEQ ID NO 24
<211> LENGTH: 27
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of formula (I).
<220> FEATURE:
<221> NAME/KEY: MISC_FEATURE
<222> LOCATION: (11)..(11)
<223> OTHER INFORMATION: Xaa at position 11 is either Lys (K) or Arg (R).
<220> FEATURE:
<221> NAME/KEY: MISC_FEATURE
<222> LOCATION: (12)..(12)
<223> OTHER INFORMATION: Xaa at position 12 is either Ala (A) or Val (V).

<400> SEQUENCE: 24

```
Gly Ser Xaa Phe Leu Ser Pro Glu His Gln Xaa Xaa Gln Gln Arg Lys
1               5                   10                  15

Glu Ser Lys Lys Pro Pro Ala Lys Leu Gln Pro
            20                  25
```

<210> SEQ ID NO 25
<211> LENGTH: 28
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of formula (I).
<220> FEATURE:
<221> NAME/KEY: MISC_FEATURE
<222> LOCATION: (11)..(11)
<223> OTHER INFORMATION: Xaa at position 11 is either Lys (K) or Arg (R).
<220> FEATURE:
<221> NAME/KEY: MISC_FEATURE
<222> LOCATION: (12)..(12)
<223> OTHER INFORMATION: Xaa at position 12 is either Ala (A) or Val (V).

<400> SEQUENCE: 25

```
Gly Ser Xaa Phe Leu Ser Pro Glu His Gln Xaa Xaa Gln Gln Arg Lys
1               5                   10                  15

Glu Ser Lys Lys Pro Pro Ala Lys Leu Gln Pro Arg
            20                  25
```

<210> SEQ ID NO 26
<211> LENGTH: 27
<212> TYPE: PRT
<213> ORGANISM: Felis catus
<220> FEATURE:
<221> NAME/KEY: MISC_FEATURE
<222> LOCATION: (3)..(3)
<223> OTHER INFORMATION: Xaa at position 3 is a modified serine of formula (I).

<400> SEQUENCE: 26

Gly Ser Xaa Phe Leu Ser Pro Glu His Gln Lys Val Gln Arg Lys Glu
1               5                   10                  15

Ser Lys Lys Pro Pro Ala Lys Leu Gln Pro Arg
            20                  25

<210> SEQ ID NO 27
<211> LENGTH: 28
<212> TYPE: PRT
<213> ORGANISM: Sus scrofa
<220> FEATURE:
<221> NAME/KEY: MISC_FEATURE
<222> LOCATION: (3)..(3)
<223> OTHER INFORMATION: Xaa at position 3 is a modified serine of formula (I).

<400> SEQUENCE: 27

Gly Ser Xaa Phe Leu Ser Pro Glu His Gln Lys Val Gln Gln Arg Lys
1               5                   10                  15

Glu Ser Lys Lys Pro Ala Ala Lys Leu Lys Pro Arg
            20                  25

<210> SEQ ID NO 28
<211> LENGTH: 28
<212> TYPE: PRT
<213> ORGANISM: Canis Lupus Familiaris
<220> FEATURE:
<221> NAME/KEY: MISC_FEATURE
<222> LOCATION: (3)..(3)
<223> OTHER INFORMATION: Xaa at position 3 is a modified serine of formula (I).

<400> SEQUENCE: 28

Gly Ser Xaa Phe Leu Ser Pro Glu His Gln Lys Leu Gln Gln Arg Lys
1               5                   10                  15

Glu Ser Lys Lys Pro Pro Ala Lys Leu Gln Pro Arg
            20                  25

<210> SEQ ID NO 29
<211> LENGTH: 28
<212> TYPE: PRT
<213> ORGANISM: Macaca Mulatta
<220> FEATURE:
<221> NAME/KEY: MISC_FEATURE
<222> LOCATION: (3)..(3)
<223> OTHER INFORMATION: Xaa at position 3 is a modified serine of formula (I).

<400> SEQUENCE: 29

Gly Ser Xaa Phe Leu Ser Pro Glu His Gln Arg Ala Gln Gln Arg Lys
1               5                   10                  15

Glu Ser Lys Lys Pro Pro Ala Lys Leu Gln Pro Arg
            20                  25

<210> SEQ ID NO 30
<211> LENGTH: 28
<212> TYPE: PRT
<213> ORGANISM: gallus gallus
<220> FEATURE:
<221> NAME/KEY: MISC_FEATURE
<222> LOCATION: (3)..(3)
<223> OTHER INFORMATION: Xaa at position 3 is a modified serine of formula (I).

<400> SEQUENCE: 30

-continued

Gly Ser Xaa Phe Leu Ser Pro Thr Tyr Lys Asn Ile Gln Gln Gln Lys
1 5 10 15

Asp Thr Arg Lys Pro Thr Ala Arg Leu His Arg Arg
20 25

<210> SEQ ID NO 31
<211> LENGTH: 28
<212> TYPE: PRT
<213> ORGANISM: Equus caballus
<220> FEATURE:
<221> NAME/KEY: MISC_FEATURE
<222> LOCATION: (3)..(3)
<223> OTHER INFORMATION: Xaa at position 3 is a modified serine of formula (I).

<400> SEQUENCE: 31

Gly Ser Xaa Phe Leu Ser Pro Glu His His Lys Val Gln His Arg Lys
1 5 10 15

Glu Ser Lys Lys Pro Pro Ala Lys Leu Lys Pro Arg
20 25

<210> SEQ ID NO 32
<211> LENGTH: 11
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE
<222> LOCATION: (3)..(3)
<223> OTHER INFORMATION: Xaa at position 3 is a modified serine of formula (I).

<400> SEQUENCE: 32

Gly Ser Xaa Phe Leu Ser Pro Glu His Gln Cys
1 5 10

<210> SEQ ID NO 33
<211> LENGTH: 17
<212> TYPE: PRT
<213> ORGANISM: Artificial
<220> FEATURE:
<223> OTHER INFORMATION: Homo sapiens or Rattus Norvegicus

<400> SEQUENCE: 33

Cys Gln Gln Arg Lys Glu Ser Lys Lys Pro Pro Ala Lys Leu Gln Pro Arg
1 5 10 15

<210> SEQ ID NO 34
<211> LENGTH: 29
<212> TYPE: PRT
<213> ORGANISM: Artificial
<220> FEATURE:
<223> OTHER INFORMATION: Homo sapiens or Rattus Norvegicus
<220> FEATURE:
<221> NAME/KEY: MISC_FEATURE,
<222> LOCATION: (3)..(3)
<223> OTHER INFORMATION: Xaa at position 3 is a modified serine of formula (I).

<400> SEQUENCE: 34

Gly Ser Xaa Phe Leu Ser Pro Glu His Gln Lys Ala Gln Gln Arg Lys
1 5 10 15

Glu Ser Lys Lys Pro Pro Ala Lys Leu Gln Pro Arg Cys
20 25

VACCINES AND METHODS FOR CONTROLLING ADIPOSITY

CROSS-REFERENCE TO RELATED APPLICATIONS

This application is a national stage filing under 35 U.S.C. 371 of International Application No. PCT/US2007/074976 filed on Aug. 1, 2007, which claims priority to U.S. Provisional Application No. 60/821,071 filed Aug. 1, 2006. These applications are incorporated herein by reference in their entireties.

This invention was made with government support under DK064871 awarded by the National Institutes of Health. The government has certain rights in the invention.

INTRODUCTION

Obesity endangers the lives of millions of people worldwide, through comorbidities such as heart disease, cancers, type 2 diabetes, stroke, arthritis, and major depression. About 1 billion people worldwide are overweight or obese (body mass index=25-30 or ≥30 kg/$m^2$, respectively), with disproportionately higher prevalence rates in affluent countries. For example, in the United States, the National Health and Nutrition Examination Survey (NHANES) found that, in 2003-2004, approximately 66% of all American adults 20 years of age or older were overweight or obese. Almost 4 out of every 5 adult men aged 40-59 were so classified. Even in children and adolescents between the ages of 6-11 and 12-19, 19% and 17%, respectively, were overweight. Alarmingly, the prevalence of obesity has tripled for adolescents in the past two decades. The increase in the number of people who are overweight or obese cuts across all ages, racial and ethnic groups, and both genders, and is increasingly global. For example, the prevalence of obesity in urban preschoolers in China climbed more than 8-fold between 1989-1997, and the rate of obesity in British adults rose almost 3-fold from 1980-2002. In 2000, more than 110,000 deaths in the United States were associated with obesity, as shown by confound-adjusted analysis of 3 NHANES cohorts, and the economic cost of obesity in the United States has been estimated to be $117 billion.

At this time, available non-surgical treatments for obesity, including drugs, are palliative and effective only while treatment is maintained. When treatments are discontinued, weight gain inevitably results. For obesity treatments to work, they must affect energy intake, absorption, expenditure or storage. While many drugs have been marketed or are currently under investigation for the treatment of obesity, several have adverse side effects, including insomnia, asthenia, fecal incontinence, hypertension, tachychardia, valvular heart abnormalities, and even death. Accordingly, several weight loss drugs have been banned by the Food and Drug Administration, including the first one approved for this indication, desoxyephedrine (1946), and more recently d-fenfluramine/fenfluramine (September, 1997) and ephedrine alkaloids (April, 2004).

Fortunately, research over the past fifteen years has revolutionized understanding of the molecular mechanisms that homeostatically control body weight and fat. Accumulated findings support a lipostatic hypothesis of energy homeostasis, in which the brain seeks to retain stored energy constant over long periods as adipose tissue. Accordingly, a highly integrated, redundant neurohumoral energy homeostasis feedback system, through behavioral and metabolic mechanisms, serves to minimize the impact of short-term fluctuations in energy balance, and especially negative energy balance, on fat mass. The identification of genes whose loss of function mutations result in monogenic obesity syndromes or confer resistance to obesity in humans or rodents have provided critical genetic entry points for characterizing the interconnected pathways that regulate energy homeostasis. The identification of these receptors and ligands has led to research efforts to target signals at both ends of the energy spectrum, however, no viable vaccine or treatment modality is yet available.

SUMMARY OF THE INVENTION

The inventors have discovered that modulating the bioavailability of the gastric endocrine hormone ghrelin via active immunization with ghrelin-derived polypeptide immunoconjugates provides a means to regulate energy balance and slow weight gain while sparing lean mass.

Accordingly, in one aspect, the invention provides an immunoconjugate which comprises a ghrelin polypeptide and a carrier moiety, wherein the ghrelin polypeptide is linked to the carrier moiety by a linker moiety. The ghrelin polypeptide immunoconjugate comprises the following sequence:

Gly-Ser-A-Phe-Leu-B-C wherein A and B are defined as follows:

A is a moiety having the following structure:

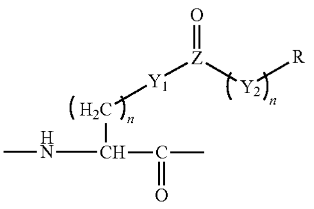

wherein: $Y_1$ and $Y_2$ are independently selected from O, $CH_2$ and NH; n is 0 or 1; Z is C, PO or SO; and R is a saturated or unsaturated, branched or unbranched, substituted or unsubstituted hydrocarbon group having about 3 to about 10 carbon atoms, or is a cycloalkyl or aryl group having about 3 to about 13 carbon atoms; and B comprises a subsequence of 0 to 23 consecutive amino acid residues of SEQ ID NO: 2; and C comprises a carrier moiety.

In another aspect, the invention provides a composition comprising an immunogenically effective amount of the immunoconjugate described above and a physiologically acceptable vehicle.

In yet another aspect, the invention provides a method of inducing an anti-ghrelin immune response in a subject comprising administering to the subject a composition comprising an immunologically effective amount of the immunoconjugate described above and a physiologically acceptable vehicle.

In a further aspect, the invention provides a method of controlling adiposity in a subject. The method encompasses administering to the subject the composition described above.

DESCRIPTION OF ILLUSTRATIVE EMBODIMENTS

Figure 1:
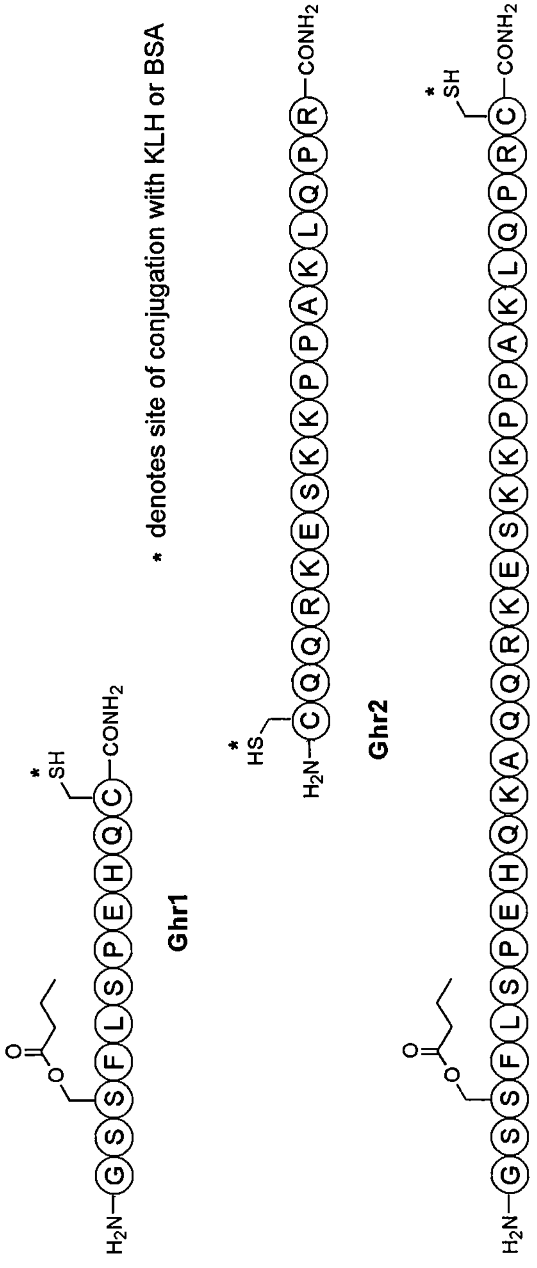
FIG. 1 depicts ghrelin-hapten immunoconjugates Ghr1 (SEQ ID NO: 32), Ghr2 (SEQ ID NO: 33) and Ghr3 (SEQ ID NO: 34) used to generate ghrelin-specific immune responses as described in the examples.

The present invention provides ghrelin polypeptide immunoconjugates, wherein the ghrelin polypeptide portion of the immunoconjugate includes a modified serine residue at the third amino acid position, as described herein. The immunoconjugates are suitably represented by the following sequence:

```
Gly-Ser-A-Phe-Leu-B-C
```

wherein A and B are defined as follows:

A is a moiety having the following structure:

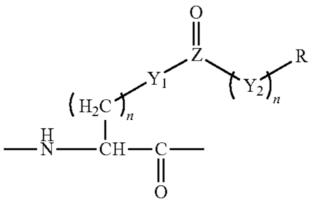

wherein: $Y_1$ and $Y_2$ are independently selected from O, $CH_2$ and NH; n is 0 or 1; Z is C, PO or SO; and R is a saturated or unsaturated, branched or unbranched, substituted or unsubstituted hydrocarbon group having about 3 to about 10 carbon atoms, or is a cycloalkyl or aryl group having about 3 to about 13 carbon atoms;

B comprises a subsequence of 0 to 23 consecutive amino acid residues of SEQ ID NO: 2; and C comprises a carrier moiety.

The immunoconjugates are suitably included in a vaccine composition with a physiologically acceptable vehicle. The invention also provides methods of inducing an anti-ghrelin immune response in a subject and controlling adiposity in a subject.

Ghrelin Polypeptides

As used herein and in the art, the term "polypeptide" refers to two or more amino acid moieties linked by amide bonds, and includes both peptides and proteins. The ghrelin polypeptides of the invention may be purified or synthetic. "Purified" refers to material that is at least partially separated from components which normally accompany it in its native state. As is appreciated by skilled artisans, purity of polypeptides is typically determined using analytical techniques such as polyacrylimide gel electrophoresis or high performance liquid chromatography. As used herein, "synthetic" refers to both recombinantly produced and prepared via solid phase techniques, as known in the art.

The ghrelin polypeptides of the invention have, at minimum, a sequence of amino acids comprising Gly Ser Xaa Phe Leu (SEQ ID NO:1), wherein A denotes a modified serine residue having a structure of formula (I):

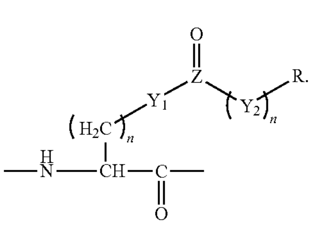

(I)

With reference to formula (I), $Y_1$ and $Y_2$ are independently selected from O, $CH_2$ and NH; and n is 0 or 1. Also in formula (I), Z is suitably selected from C, PO or SO. R is a saturated or unsaturated, branched or unbranched, substituted or unsubstituted hydrocarbon group having about 3 to about 10 carbon atoms, or is a cycloalkyl or aryl group having about 3 to about 13 carbon atoms. As used herein, as "hydrocarbon group" refers to an aliphatic hydrocarbon group having a specified number of carbon atoms in the chain. The hydrocarbon group may comprise, e.g., an alkyl, an alkenyl or alkynyl group. In a particularly suitable embodiment, $Y_1$ is O, Z is C, n is 0, and R is $-CH_2CH_2CH_3$. In sequence listings detailed below, A is identified as Xaa.

The ghrelin polypeptide may further comprise B, where B is a carboxy-terminal subsequence of the full length ghrelin polypeptide. The subsequence includes any of SEQ ID NO: 2 or the full sequence of SEQ ID NO:2. In other words, the ghrelin polypeptide comprises SEQ ID NO: 1 and a sequence or subsequence of SEQ ID NO: 2. For example, the full ghrelin polypeptide sequence may comprise any of the following sequences:

```
                                        (SEQ ID NO: 1)
Gly Ser Xaa Phe Leu;

                                        (SEQ ID NO: 3)
Gly Ser Xaa Phe Leu Ser;

                                        (SEQ ID NO: 4)
Gly Ser Xaa Phe Leu Ser Pro;

                                        (SEQ ID NO: 5)
Gly Ser Xaa Phe Leu Ser Pro Glu;

                                        (SEQ ID NO: 6)
Gly Ser Xaa Phe Leu Ser Pro Glu His;

                                        (SEQ ID NO: 7)
Gly Ser Xaa Phe Leu Ser Pro Glu His Gln;

                                        (SEQ ID NO: 8)
Gly Ser Xaa Phe Leu Ser Pro Glu His Gln Lys/Arg;

                                        (SEQ ID NO: 9)
Gly Ser Xaa Phe Leu Ser Pro Glu His Gln Lys/Arg
Ala/Val;

                                       (SEQ ID NO: 10)
Gly Ser Xaa Phe Leu Ser Pro Glu His Gln Lys/Arg
Ala/Val Gln;
```

-continued (SEQ ID NO: 11)
Gly Ser Xaa Phe Leu Ser Pro Glu His Gln Lys/Arg
Ala/Val Gln Gln;

(SEQ ID NO: 12)
Gly Ser Xaa Phe Leu Ser Pro Glu His Gln Lys/Arg
Ala/Val Gln Gln Arg;

(SEQ ID NO: 13)
Gly Ser Xaa Phe Leu Ser Pro Glu His Gln Lys/Arg
Ala/Val Gln Gln Arg Lys;

(SEQ ID NO: 14)
Gly Ser Xaa Phe Leu Ser Pro Glu His Gln Lys/Arg
Ala/Val Gln Gln Arg Lys Glu;

(SEQ ID NO: 15)
Gly Ser Xaa Phe Leu Ser Pro Glu His Gln Lys/Arg
Ala/Val Gln Gln Arg Lys Glu Ser;

(SEQ ID NO: 16)
Gly Ser Xaa Phe Leu Ser Pro Glu His Gln Lys/Arg
Ala/Val Gln Gln Arg Lys Glu Ser Lys;

(SEQ ID NO: 17)
Gly Ser Xaa Phe Leu Ser Pro Glu His Gln Lys/Arg
Ala/Val Gln Gln Arg Lys Glu Ser Lys Lys;

(SEQ ID NO: 18)
Gly Ser Xaa Phe Leu Ser Pro Glu His Gln Lys/Arg
Ala/Val Gln Gln Arg Lys Glu Ser Lys Lys Pro;

(SEQ ID NO: 19)
Gly Ser Xaa Phe Leu Ser Pro Glu His Gln Lys/Arg
Ala/Val Gln Gln Arg Lys Glu Ser Lys Lys Pro Pro;

(SEQ ID NO: 20)
Gly Ser Xaa Phe Leu Ser Pro Glu His Gln Lys/Arg;
Ala/Val Gln Gln Arg Lys Glu Ser Lys Lys Pro Pro
Ala;

(SEQ ID NO: 21)
Gly Ser Xaa Phe Leu Ser Pro Glu His Gln Lys/Arg
Ala/Val Gln Gln Arg Lys Glu Ser Lys Lys Pro Pro
Ala Lys;

(SEQ ID NO: 22)
Gly Ser Xaa Phe Leu Ser Pro Glu His Gln Lys/Arg
Ala/Val Gln Gln Arg Lys Glu Ser Lys Lys Pro Pro
Ala Lys Leu;

(SEQ ID NO: 23)
Gly Ser Xaa Phe Leu Ser Pro Glu His Gln Lys/Arg
Ala/Val Gln Gln Arg Lys Glu Ser Lys Lys Pro Pro
Ala Lys Leu Gln;

(SEQ ID NO: 24)
Gly Ser Xaa Phe Leu Ser Pro Glu His Gln Lys/Arg
Ala/Val Gln Gln Arg Lys Glu Ser Lys Lys Pro Pro
Ala Lys Leu Gln Pro;
or

-continued (SEQ ID NO: 25)
Gly Ser Xaa Phe Leu Ser Pro Glu His Gln Lys/Arg
Ala/Val Gln Gln Arg Lys Glu Ser Lys Lys Pro Pro
Ala Lys Leu Gln Pro Arg, wherein Xaa is A, the modified serine as defined above. It is also specifically contemplated that any of the above-listed amino acids may be replaced by a suitable unnatural amino acid, e.g., as described in Chemistry and Biochemistry of Amino Acids, Peptides and Proteins, Vol. 7, ed. B. Weinstein (1983), incorporated herein by reference.

It is also contemplated that the ghrelin peptide sequence will correspond to the sequence of ghrelin specific to the species to be immunized, and having the modified serine at position 3 as described herein. It is contemplated since the sequences between species is conserved and has only slight variations, cross-reactivity between peptides and species is contemplated.

Carrier Moieties

The immunoconjugates of the invention comprise the above-described ghrelin polypeptides covalently or non-covalently conjugated to C, a carrier moiety, using standard methods known in the art. A "carrier moiety," as used herein, refers to a conjugation partner capable of enhancing the immunogenicity of a polypeptide. For instance, polymers can be used, e.g. carbohydrates such as dextran, mannose or mannan. Integral membrane proteins from, e.g., *E. coli* and other bacteria are also useful conjugation partners. The traditional carrier molecules such as keyhole limpet hemocyanin (KLH), tetanus toxoid, diphtheria toxoid, and bovine serum albumin (BSA) are also suitable.

Linking Moieties

As is known in the art, there is a wide range of available methods for linking polypeptides to carrier moieties, any of which are suitably adapted for use with the invention. Most strategies involve conjugating the polypeptide to a derivatized molecule on the carrier moiety via formation of a covalent bond between reactive groups on the polypeptide and carrier. Suitably, one or more amino acids having a reactive group incorporated in the ghrelin polypeptide sequence is used to link the polypeptide to the carrier moiety. Suitable linking moieties are those having amino groups, carboxyl groups or sulfhydryl groups. As will be appreciated, functional groups of amino acids in the sequence of the ghrelin polypeptide may be used as a linking moiety to couple the polypeptide to the carrier. Such amino acids may include lysine, arginine, cysteine, aspartate, glutamate, tyrosine and/or histidine. Disulfide coupling using cysteine residues outside the antibody binding domain of the ghrelin polypeptide is one particularly suitable coupling strategy, wherein the cysteine is suitably introduced using standard recombinant technology. In one embodiment, a cysteine residue is positioned at a terminus of the ghrelin polypeptide, e.g., the carboxy or amino terminus.

Additional suitable means of linking polypeptide moieties to carriers are known in the art and may be used with the present invention.

Immunogenic Compositions

Ghrelin immunoconjugates, as described above, are suitably included in an immunogenically effective amount in a composition with a physiologically acceptable vehicle. An "immunogenically effective amount," as used herein and in the art, is an amount of an immunoconjugate which is capable of inducing an immune response which significantly engages agents which share immunological features with the immunogen, i.e., native, endogenous ghrelin. A "physiologically acceptable" vehicle is any vehicle that is suitable for in vivo administration (e.g., oral, transdermal or parenteral administration) or in vitro use, i.e., cell culture.

Suitably, compositions comprising ghrelin immunoconjugates of the invention may be formulated for in vivo use, i.e., therapeutic or prophylactic administration to a subject. In particular embodiments, the compositions are formulated as vaccine compositions. As used herein, a "vaccine" is a composition that is capable of inducing an immune response in a subject, including but not limited to, the production of sequestering antibodies.

Preparation of vaccines which contain polypeptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables, either as liquid solutions or suspensions; solid forms suitable for formulation in solution or suspension prior to injection may also be prepared. The preparation may also be emulsified. The ghrelin immunoconjugate may be mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines, as described below.

The vaccines are conventionally administered parenterally, by injection, for example, subcutaneously, intracutaneously, intradermally, subdermally or intramuscularly. Additional formulations which are suitable for other modes of administration include suppositories and, in some cases, oral, buccal, sublinqual, intraperitoneal, intravaginal, anal, epidural, spinal, and intracranial formulations. For suppositories, traditional binders and carriers may include, for example, polyalkalene glycols or triglycerides; such suppositories may be formed from mixtures containing the active ingredient in the range of 0.5% to 10%, preferably 1 to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10 to 95% of active ingredient, preferably 25 to 70%.

As is appreciated, vaccines are administered in a manner compatible with the dosage formulation, and in such amount as will be prophylactically or therapeutically effective and immunogenic. The quantity to be administered depends on the subject to be treated, including, e.g., the capacity of the individual's immune system to mount an immune response, and the degree of protection desired. Suitable dosage ranges are from about 0.1 μg/kg body weight to about 10 mg/kg body weight, such as in the range from about 500 μg/kg body weight to about 1000 μg/kg body weight. Suitable regimens for initial administration and booster shots are also contemplated and are typified by an initial administration followed by subsequent inoculations or other administrations. Some embodiments of the ghrelin immunoconjugate vaccine of the invention are sufficiently immunogenic, but for some of the others, the immune response will be enhanced if the vaccine further comprises an adjuvant substance. Adjuvants and their use are well known in the art. The term "adjuvant" refers herein to a substance which is 1) not in itself capable of mounting an immune response against the immunoconjugate of the vaccine, but which is 2) nevertheless capable of enhancing the immune response against the immunoconjugate. Various methods of achieving an adjuvant effect are known. General principles and methods are detailed in "The Theory and Practical Application of Adjuvants", 1995, Duncan E. S. Stewart-Tull (ed.), John Wiley & Sons Ltd, ISBN 0-471-95170-6, and also in "Vaccines: New Generation Immunological Adjuvants", 1995, Gregoriadis G et al. (eds.), Plenum Press, New York, ISBN 0-306-45283-9, both of which are hereby incorporated by reference herein. A particularly suitable adjuvant for use with the invention is aluminium hydroxide or phosphate (alum), commonly used as 0.05 to 0.1 percent solution in buffered saline.

Methods of Inducing Anti-Ghrelin Immune Response

Some embodiments of the invention provide a method of inducing an anti-ghrelin immune response in a subject. A "subject" is a vertebrate, suitably a mammal, more suitably a human. Suitable subjects may also include domestic animals, e.g., cats, dogs and horses. As will be appreciated, for purposes of study, the subject is suitably an animal model, e.g., a mouse or rat. It will be appreciated that for other species, e.g., dog, cat, horse or mouse, the ghrelin polypeptide portion of the immunoconjugate can be selected based on species. As used herein, an "anti-ghrelin immune response" specifically refers to inducing a therapeutic or prophylactic ghrelin-sequestering effect that is mediated by the immune system of the subject. Such an immune response suitably promotes clearance or immune control of endogenous ghrelin in the subject such that system-wide effects are observed in the subject, e.g., prevention or slowing of weight gain, sparing of lean body mass, decreased feed efficiency and decreased relative adiposity.

An anti-ghrelin immune response is suitably assessed by the assays described in the examples below. Inducing an anti-ghrelin immune response in a subject in accordance with the invention may be accomplished by administering to the subject the ghrelin immunoconjugate compositions described above.

Methods of Controlling Adiposity

Some embodiments of the invention provide a method of controlling adiposity in a subject. "Controlling adiposity," as used herein, includes, but is not limited to, preventing or slowing of weight gain, sparing lean body mass, decreasing feed efficiency and decreasing relative adiposity in the subject. Methods of controlling adiposity may be accomplished by administering to the subject the ghrelin immunoconjugate compositions described above. Most suitably, the invention prevents the development of obesity in the subject.

Administration to a subject of the ghrelin immunoconjugate compositions in accordance with the invention appears to exhibit beneficial effects in a dose-dependent manner. Thus, within broad limits, administration of larger quantities of the ghrelin immunoconjugate compositions is expected to control adiposity to a greater degree than does administration of a smaller amount. Moreover, efficacy is also contemplated at dosages below the level at which toxicity is seen. Further, in practice, higher doses are generally used where the therapeutic treatment of obesity is the desired end, while the lower doses are generally used for prophylactic purposes or slowing weight gain.

It will be appreciated that the specific dosage administered in any given case will be adjusted in accordance with the condition of the subject and other relevant medical factors that may modify the activity of the ghrelin immunoconjugate or the response of the subject, as is well known by those skilled in the art. For example, the specific dose for a particular patient depends on age, body weight, general state of health, diet, the timing and mode of administration, the rate of excretion and medicaments used in combination. Dosages for a given patient can be determined using conventional considerations such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. It is anticipated that dosages of immunoconjugate in the range from about 0.1 μg/kg body weight to about 10 mg/kg body weight are contemplated, such as in the range from about 500 μg/kg body weight to about 1000 μg/kg body weight, will prevent or reduce symptoms at least 50% compared to pre-treatment symptoms. It is specifically contemplated that vaccine preparations and compositions of the invention may palliate or alleviate weight gain without providing a cure, or, in some embodiments, may be used to cure or prevent obesity.

It is specifically contemplated that any embodiment of any method or composition of the invention may be used with any other method or composition of the invention.

As used in this specification and the appended claims, the singular forms "a," "an," and "the" include plural referents unless the content clearly dictates otherwise. Thus, for example, reference to a composition containing "a polypeptide" includes a mixture of two or more polypeptides. It should also be noted that the term "or" is generally employed in its sense including "and/or" unless the content clearly dictates otherwise.

It also is specifically understood that any numerical value recited herein includes all values from the lower value to the upper value, i.e., all possible combinations of numerical values between the lowest value and the highest value enumerated are to be considered to be expressly stated in this application. For example, if a range is stated as 1% to 50%, it is intended that values such as 2% to 40%, 10% to 30%, or 1% to 3%, etc., are expressly enumerated in this specification.

EXAMPLES

The following examples are provided to assist in a further understanding of the invention. The particular materials and conditions employed are intended to be further illustrative of the invention and are not limiting on the reasonable scope of the appended claims.

Example 1

Ghrelin Hapten Immunoconjugate Synthesis

Ghr1-Ghr3 were synthesized and coupled to the carrier protein keyhole limpet hemocyanin (KLH), yielding immunoconjugates Ghr1-KLH, Ghr2-KLH and Ghr3-KLH. For peptide synthesis, all haptens and substrates were prepared on a 1.0 mmol scale as C-terminal amides using custom-written DIC/HOBt protocols for Fmoc/tBu SPPS on a CS Bio 136 automated peptide synthesizer. For peptides bearing Ser-3 side-chain esterification, 10 mmol of the requisite acid was preactivated with 5 mmol DIC in 10 mL DCM for 20 min, after which 10 mL DMF was added. The resulting slurry was added to the partially protected peptide-resin, followed by 0.5 mmol DMAP, and mixed by orbital shaking overnight. Test TFA cleavages were used to verify quantitative acylation, For Lys(Mca) conjugations, the peptide-resin was shaken with 0.2 eq. $Pd(PPh_3)_4$ and 10 eq. N,N'-dimethylbarbituric acid in 1:1 DMF:DCM for 12 hrs. The newly-unmasked free-amine was then neutralized by treatment with 5% DIEA/DMF, after which 7-methoxycoumarinyl-4-acetic acid was coupled according to standard DIC/HOBt protocols. For n-butanoic acid conjugations, 5 mmol n-butanoic acid was preactivated with 5 mmol DIC in 10 mL DCM for 20 min, after which 10 mL DMF was added. The resulting slurry was added to the protected peptide-resin, followed by 0.5 mmol DMAP, allowed to react for 1 h, and the entire procedure performed twice to achieve quantitative n-butanoylation. After washing with DMF and DCM (2×20 sec flow wash each), the completed peptide-resins were dried in vacuo overnight. Global deprotection and cleavage were accomplished by batch-wise treatment with 95:2.5:2.5 TFA:water:triisopropylsilane (TIPS) for 2 hrs, followed by filtration and removal of TFA by rotary evaporation. Peptides were then triturated from 10 volumes of $Et_2O$ (pre-chilled at −20° C.) and isolated by centrifugation. After likewise washing the pellet two times further with $Et_2O$, peptides were extracted into 50% AcOH and purified by RP-HPLC directly.

Ghrelin(1-10) Ser-3(butanoyl) hapten, Ghr1. ESI-MS: Theory, MW=1406.4; $M^{1+}$=1407.4, $M^{2+}$=704.2. Observed, $M^{1+}$=1408.3, $M^3$+=704.0.

Ghrelin(13-28) hapten, Ghr2. ESI-MS: Theory, MW=2166.5; $M^2$+1084.3, $M^3$+=723.2. Observed, $M^2$+=1084.5, $M^3$+=723.2

Rat ghrelin(1-28) Ser-3(butanoyl) hapten, Ghr3. ESI-MS: Theory, MW=3506.0; $M^{2+}$=1754.0, $M^3$+=1169.7. Observed, $M^2$+=1754.1, $M^3$+=1169.7.

Example 2

Subjects and Vaccination Protocol

Mature male Wistar rats (n=17, M+SEM: 413+8 g at onset, 502+12 g by $4^{th}$ immunization; Charles River, Hollister, Calif.) were individually housed in a 12 h:12 h lit (0600h lights on), humidity- (60%) and temperature-controlled (22° C.) vivarium with continuous access to chow and water. The pelleted chow diet (LM-485 Diet 7012; Harlan Teklad, Madison, Wis., USA) is a corn-based, extruded cereal comprised of 65% carbohydrate, 13% fat, 21% protein, metabolizable energy 3.41 kcal/g. Procedures adhered to the National Institutes of Health Guide for the Care and Use of Laboratory Animals (NIH Publication number 85-23, revised 1996) and the "Principles of laboratory animal care" (http://www.nap.edu/readingroom/bookslabrats) and were approved by the Institutional Animal Care and Use Committee of The Scripps Research Institute.

Age- and weight-matched mature rats were immunized using protocols of our laboratory as described in Qi et al., $\Delta^9$-Tetrahydrocannabinol immunochemical studies: Haptens, monoclonal antibodies, and a convenient synthesis of radiolabeled $\Delta^9$-Tetrahydrocannabinol, Journal of Medical Chemistry, (2005), 48:7389-7399, incorporated herein by reference. Immunization involved 5 immunizations over 12 weeks. Age and weight-matched rats received immunizations (i.p. 0.4 ml) 90 min before the dark cycle on experimental days 0, 21, 35, 56 and 84. The first 3 immunizations consisted of Ribi MPL-TDM emulsion adjuvant (RIBI Immunochemical Research Inc.) containing 250 μg of Ghr1-KLH, Ghr2-KLH, Ghr3-KLH or KLH in 100 mM PBS, pH 7.4. The last two used alum (Pierce) as the adjuvant. Tail blood was collected 1 week post-immunization, centrifuged, and plasma analyzed for antibody titers and ghrelin binding affinity.

Example 3

Plasma Vaccine Antibody Titers and Ghrelin Binding Affinity in Vaccinated Rats Rats were vaccinated as described in Example 2. Plasma antibody titers were determined by ELISA. ELISA plates (96-well, COSTAR 3590) containing 3 ng per well Ghr3-BSA in 50 μL of 10 mM PBS, pH 7.2, were dried overnight, followed by routine ethanol fixing and blocking with blotto (non-fat milk) in PBS. Rat plasma samples were serially diluted beginning with a 1:100 dilution in blotto. Plasma binding was allowed to take place for 1 hour in a moist chamber at 37° C. After washing, 200 ng per well goat anti-rat IgG conjugated with alkaline phosphatase (Southern Biotech) in 50 μL PBS-blotto was added and incubated for 1 h in a moist chamber at 37° C. The plates were thoroughly washed with water, air dried and developed by adding 200 μL per well of 200 μM p-nitrophenylphosphate (Pierce) in 100 mM 4-morpholinepropanesulphonic acid (MOPS), pH 7.4. After 3 hours at room temperature, the absorbance was measured at 405 nm in a microplate reader (Molecular Devices). Results are shown in Table 1, below.

Ghrelin specificity of plasma was determined using two assays: an equilibrium dialysis assay and a competition ELISA. Equilibrium dialysis was performed using serial dilutions of [$^{125}$I]-rat ghrelin (Ser-3-n-octanoyl, Bachem, diluted in situ with non-labeled ghrelin) as ligand and constant plasma amounts (1:1 dilution in PBS, pH 7.4). Wells in one microtiter plate (12 per sample) were filled with 170 μL of radiolabeled ghrelin in PBS, and a second plate was prepared with wells containing plasma of rats (that were immunized with the ghrelin-KLH immunoconjugates or with just KLH) in PBS (170 μL/well). The two plates were tightly connected with filled wells facing each other and separated with a dialysis membrane (cutoff 14,000 Da). The plates were attached vertically to a shaker and were shaken for 24 h at room temperature, after which they were carefully separated. The membrane was discarded and from each well 100 μl was transferred to tubes for γ-radiation counting. The average in differences in DPM (disintegrations per minute) between opposite wells was determined for each dilution of ghrelin, yielding apparent binding constants ($K_{d\text{-}app}$). Results are shown in Table 1, below.

For competition ELISA, plates (96-well) were coated overnight at 4° C. with freshly prepared ghrelin-BSA conjugate. The plates were blocked with 4% skim milk, washed and plasma samples were added at appropriate dilutions. The plates were washed and Ser-3 n-octanoyl ghrelin was added to the wells in a concentration series starting at 100 μM. Plates were incubated for 1 h at 37° C., thoroughly washed, and goat anti-mouse-horseradish peroxidase (HRP) conjugate (Pierce) was added. After an incubation period of 1 h at RT, plates were thoroughly washed again and the HRP substrate (TMB substrate kit; Pierce) was added, the reaction was allowed to develop for 15 min and stopped by the addition of 2 M $H_2SO_4$. The absorbance (450 nm) was read and the values plotted using GraFit (Erithacus Software Ltd). The free antigen concentration at which the absorbance value is 50% of the maximum absorbance was considered the average $K_{D\text{-}app}$ of the plasma for ghrelin. Results are shown in Table 1, below:

TABLE 1

| | Vaccine Titers (×100) | | Plasma affinity ($K_{D\text{-}app}$) after 13 weeks for n-octanoyl ghrelin | | des-octanoyl ghrelin | Selectivity Ratio |
|---|---|---|---|---|---|---|
| Immunization group | 9 weeks | 13 weeks | ELISA (nM) | Equilibrium dialysis (nM) | ELISA (nM) | ($K_{D\text{-}app\text{-}des\text{-}octanoyl}$/ $K_{D\text{-}app\text{-}n\text{-}octanoyl}$) |
| Ghr1-KLH (n = 5) | 11 ± 3 | 34 ± 12 | 1461 ± 569 | 45 ± 22 | 47,655 ± 235 | 98 ± 48 |
| Ghr2-KLH (n = 4) | 23 ± 12 | 13 ± 3 | >50,000 | >20,000 | 14,308 ± 11,916 | <0.3 ± 0.2 |
| Ghr3-KLH (n = 5) | 56 ± 15 | 137 ± 51 | 619 ± 173 | 243 ± 192 | 26,010 ± 10,201 | 41 ± 12 |
| KLH (n = 3) | 2 ± 1 | 2 ± 1 | >50,000 | >20,000 | >50,000 | N.D. |

Data are expressed as M ± SEM. Titers and plasma affinity were log-transformed to calculate averages, selectivity ratios and for statistical analysis. Values reflect antilog transformations.

As shown in Table 1, both Ghr1-KLH and Ghr3-KLH ghrelin immunoconjugates produced good immune responses (increased vaccine antibody titers) by week 9, or after the fourth immunization. Responses were of appropriate specificity, as antibodies elicited by Ghr1-KLH did not cross-react with Ghr2-BSA, and antibodies elicited by Ghr2-KLH likewise had low affinity for Ghr1-BSA (data not shown) Although each immunization group raised an immune response against the immunoconjugate with which they were vaccinated, only rats from groups immunized with Ghr1-KLH or Ghr3-KLH developed good plasma binding affinity for n-octanoylated ghrelin, the putatively active circulating form. Plasma from rats vaccinated with Ghr1-KLH or Ghr3-KLH was not potently bound by the inactive, des-octanoyl form of ghrelin which predominates in circulation (at least 1.8:1 ratio) (Sato et. al., Molecular forms of hypothalamic ghrelin and its regulation by fasting and 2-deoxy-d-glucose administration (2005), Endocrinology, 146:2510-6, incorporated by reference) and might otherwise compete for neutralizing antibody, resulting in greater specificity for acyl vs. des-acyl ghrelin.

Example 4

Post-Immunization Weight Gain, Food Intake and Feed Efficiency

Rats were immunized as described in Example 2. Body weight and food intake were determined daily (0.1 g precision), 2 h prior to the onset of the dark cycle during the weeks after the fourth and fifth immunization, by when antibody titers maximized. Feed efficiency was calculated as body weight gained per unit energy intake (mg/kcal).

Figure 2:
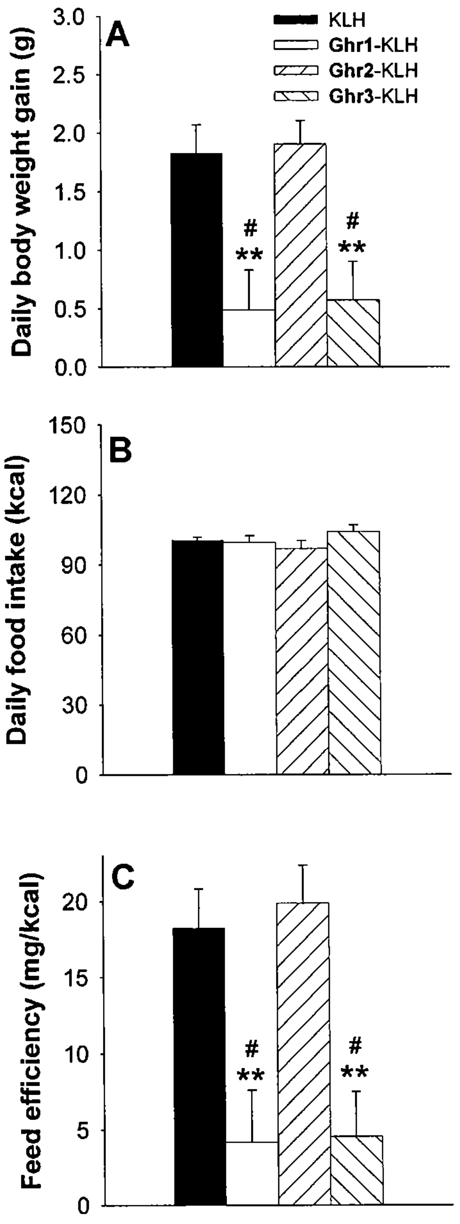
FIG. 2 graphically represents the effects of vaccination with ghrelin-hapten immunoconjugates on whole body energy homeostasis, as a function of daily body weight gain (Panel A), daily food intake (Panel B) and feed efficiency (Panel C).

FIG. 2 shows the corresponding rate of body weight gain, daily food intake and feed efficiency of immunized rats as a function of the vaccine that subjects received, once titers of several rats had increased into the 1:10,000 range. Rats that received the Ghr1-KLH and Ghr3-KLH immunoconjugates gained less weight per day than did rats immunized with Ghr2-KLH or KLH across the 7 day observation period after the $4^{th}$ immunization (FIG. 2A). This occurred despite rats eating (FIG. 2B) and drinking (not shown) normally, indicating a reduced feed efficiency of Ghr1-KLH and Ghr3-KLH-vaccinated subjects (FIG. 2C). Prior to this time, during weeks 5-8, when titers were modest and still rising, vaccine-related differences in daily weight gain (KLH: 1.22±0.32 vs. Ghr3-KLH: 0.92±0.12 and Ghr1-KLH: 1.01±0.15 g/day) and feed efficiency (KLH: 44.4±5.5 vs. Ghr3-KLH: 28.5±3.0 and Ghr1-KLH: 33.6±4.4 mg/kcal) were in the same direction, but correspondingly smaller, supporting the proposed dependence on anti-ghrelin plasma binding affinity.

Example 5

Figure 3:
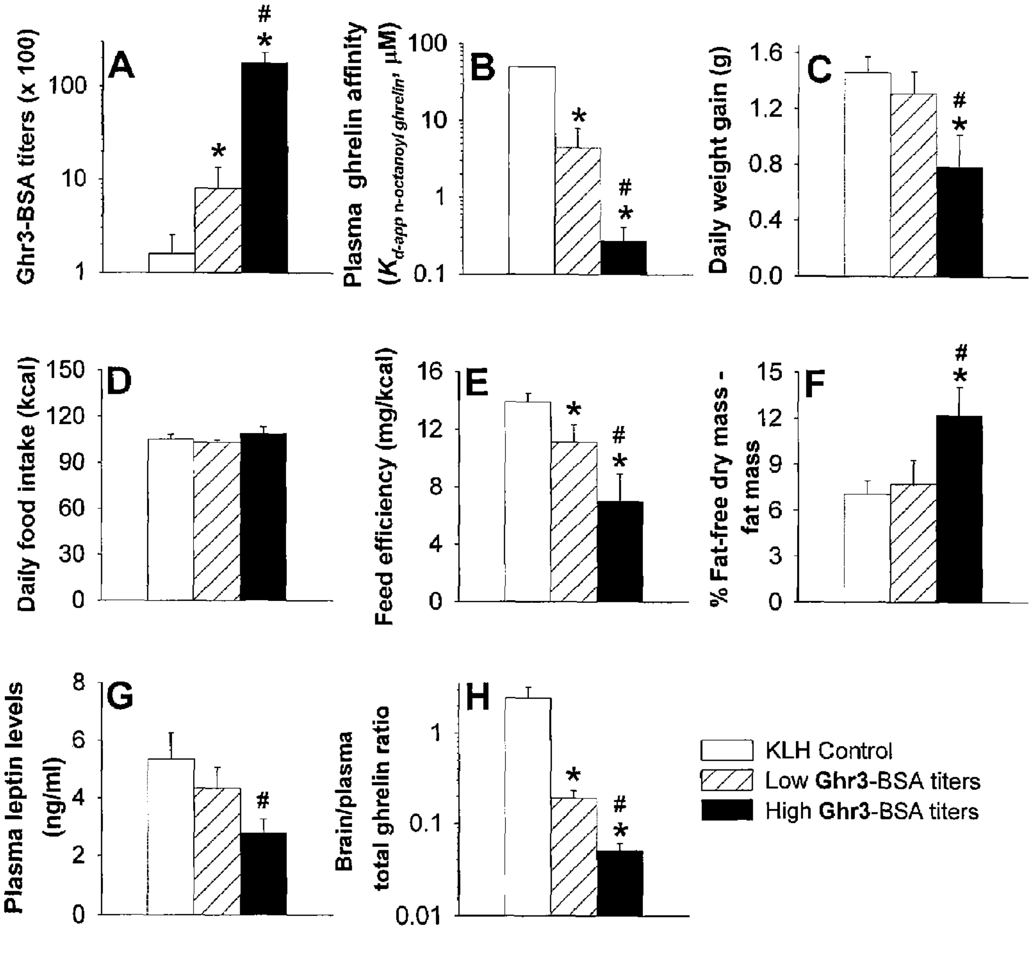
FIG. 3 graphically represents the relationship of plasma anti-ghrelin binding capacity to whole body energy homeostasis, adiposity and brain/plasma ghrelin ratios, as demonstrated by comparisons of high and low plasma titer subjects (Panel A) in terms of plasma affinity (Panel B), daily weight gain (Panel C), daily food intake (Panel D), feed efficiency (Panel E), relative fat-free dry mass (Panel F), plasma leptin levels (Panel G) and brain/plasma total ghrelin ratio (Panel G).

Relation of Plasma Anti-Ghrelin Binding Capacity to Whole Body Energy Homeostasis, Adiposity and Brain/Plasma Ghrelin Ratios To determine whether circulating anti-ghrelin binding capacity is related to the attenuation of body weight gain, subjects vaccinated as described in Example 2 were divided into those which developed high or low antibody titers to Ghr3-BSA (FIG. 3, panel A) and compared in the weeks after the $4^{th}$ and $5^{th}$ immunizations. As shown in FIG. 3, panel B, each subject with high Ghr3-BSA titers also exhibited good plasma affinity for n-octanoyl ghrelin per competition ELISA analysis ($K_{D-app}$<650 nM), more than one order greater on average than those with lower Ghr3-BSA titers. Those rats with higher plasma ghrelin binding capacity gained ~0.5 g less weight per day than those with lower plasma affinity for ghrelin (shown in FIG. 3, panel C), despite normal food intake (FIG. 3, panel D), again indicating decreased feed efficiency (FIG. 3, panel E), with the same profile of results observed after each immunization. Even rats with lower, but measurable, plasma ghrelin binding capacity exhibited reduced feed efficiency compared to KLH controls (FIG. 3, panel E).

Gastrointestinal tracts were removed from thawed (25° C.) carcasses. The carcass was then dried (70° C.) to constant mass to determine water content and then extracted with petroleum ether in a Soxhlet apparatus to determine fat-free dry mass, comprised of both protein and ash, as compared to fat mass. (Dobush et. al., (1985), Canadiaon Journal of Zoolology, 63:1917-1920, incorporated herein by reference). As shown in FIG. 3, panel F and Table 2, below, carcass analysis showed that rats with strong anti-ghrelin responses gained fat-free dry mass preferentially over fat mass, as compared to those with weaker anti-ghrelin immune responses, and did not differ in water content.

TABLE 2

| | Fat-Free Dry Mass (%) | | | Fat Mass | Water |
|---|---|---|---|---|---|
| Group | Protein | Ash | Total | (%) | (%) |
| High Ghr3-BSA titers (n = 5) | 22.9 ± 0.2* | 2.9 ± 0.1 | 25.8 ± 0.2* | 13.6 ± 1.6# | 60.6 ± 1.4 |
| Low Ghr3-BSA titers (n = 9) | 22.0 ± 0.4 | 2.8 ± 0.1 | 24.8 ± 0.4 | 17.1 ± 1.3 | 58.2 ± 1.0 |

Data are expressed as M ± SEM.

*$p < 0.05$,

#$p = 0.06$ vs. Low Ghr3-BSA titer group, Welch's corrected t-test.

Total ghrelin (octanoyl and des-octanoyl combined) concentrations in plasma and brain samples of rats were determined with use of a ghrelin enzyme immunoassay kit (Phoenix Pharmaceuticals, Belmont, Calif.). Tissue extracts were obtained following methods described by Shibata et al.; (48) >95% recovery of ghrelin was reported). Briefly, whole brains were snap-frozen in dry-ice chilled 2-methylbutane and stored at −80° C. prior to use. Brain tissue was diced into 10-15 pieces and boiled for 7 min. in water (10 mL), and acetic acid (580 μL, 100%) was added after cooling to yield 1 M AcOH. The suspension was homogenized with a Tekmar Tissumizer and centrifuged at 10,000 rpm for 10 min. Supernatant was lyophilized, redissolved in EIA buffer (Phoenix Pharmaceuticals) and analyzed following manufacturer's instructions. Consistent with the relative decrease in fattiness, terminal plasma levels of the adipocyte hormone leptin were reduced in rats with strong plasma affinity for ghrelin (FIG. 3, panel G). Circulating insulin levels did not differ reliably as a function of the plasma ghrelin binding affinity achieved (M+SEM: High: 0.8±0.2 vs. Low: 1.3±0.2 ng/ml). Possibly consistent with a reduced passage of circulating ghrelin to the central compartment, the ratio of brain/plasma levels of total ghrelin was reduced in rats in relation to their plasma anti-ghrelin binding capacity (FIG. 3, panel H).

Example 6

Plasma Levels of Inflammatory Mediators in Vaccinated Rats

To examine the possibility that vaccination effects might result from a non-specific systemic immune response, proinflammatory mediators, including interleukin-1β, interleukin-6, tumor necrosis factor-α, monocyte chemoattractant protein-1, and total plasminogen activator inhibitor type-1, were measured in rats vaccinated as described in Example 2.

Rats were sacrificed by decapitation on experimental day 92 1-4 hr into the dark cycle, and trunk blood was collected on chilled polypropylene tubes containing 0.5 M EDTA (~1/10 v/v) and protease inhibitor cocktail (~1/100 v/v) (Sigma, St. Louis, Mo.). Plasma was obtained by centrifugation (3000 rpm, 4° C., 20 min) and stored at −80° C. until analysis by a multiplex rat adipokine panel (Linco, St. Charles, Mo.), an xMAP™ technology-based immunoassay using Luminex® instrumentation. The limit of sensitivity for TNF-α, MCP-1 and IL-1β was 4.9 pg/ml and for leptin, IL-6, insulin and total PAI-1 was 12.2 pg/ml. The typical intra-assay coefficient of variation is <4%.

As shown in Table 3, below, plasma levels were low on an absolute basis across treatment groups and unrelated to plasma specificity for acylated ghrelin.

TABLE 3

| | | | IL-6 | | TNF-α | | MCP-1 | |
|---|---|---|---|---|---|---|---|---|
| Group | IL-1β pg/ml | Total PAI-1 pg/ml | Detect-able | pg/ml | Detect-able | pg/ml | Detect-able | pg/ml |
| High Ghr3-BSA titers (n = 5) | 18 ± 8 | 452 ± 315 | 2/5 | 101 ± 70 | 0/5 | <4.9 | 3/5 | 177 ± 158 |
| Low Ghr3-BSA titers (n = 9) | 38 ± 8 | 220 ± 88 | 3/9 | 157 ± 90 | 1/9 | 7 ± 2 | 4/9 | 79 ± 32 |
| KLH (n = 3) | 27 ± 11 | 266 ± 210 | 2/3 | 221 ± 123 | 0/3 | <4.9 | 1/3 | 30 ± 25 |

Data are expressed as M ± SEM or as the frequency of detectable levels.

Example 7

Statistics

Analyses of variance (ANOVA) were used to identify group differences. Fisher's protected LSD tests were used for posthoc comparisons. Welch's t-tests, corrected for multiple comparisons, were used to compare groups with unequal variance. To reduce heterogeneity of variance and achieve a more normal distribution, data for IL-6, TNF-α, total PAI-1, MCP-1, plasma antibody titers, apparent ghrelin binding affinity constants of plasma, and brain/plasma total ghrelin ratios were first log-transformed for statistical analysis, including calculation of titer selectivity ratios. Corresponding values presented in tables or figures represent antilog transformations. Chi-square analysis was used to test whether subjects differed in the frequency of having detectable circulating cytokine levels. The software package was Systat 11.0 (SPSS, Chicago, Ill., USA).

We claim:

1. An immunoconjugate comprising:

a) a ghrelin polypeptide comprising Gly-Ser-A-Phe-Leu-B, wherein:

A comprises:

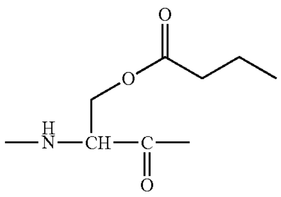

;

B comprises a subsequence of 0 to 23 consecutive amino acid residues of SEQ ID NO: 2; and b) a carrier moiety, wherein the carrier moiety is selected from the group consisting of dextran, mannose, mannan, integral membrane proteins from, *E. coli* and other bacteria, keyhole limpet hemocyanin (KLH), tetanus toxoid, diphtheria toxoid, and bovine serum albumin (BSA), wherein the ghrelin polypeptide is linked at its carboxy terminus to the carrier moiety by a linker moiety, wherein the linker moiety forms a covalent bond between reactive groups on the polypeptide and carrier moiety.

2. The immunoconjugate of claim 1, wherein B comprises amino acid residues 1 to 5 of SEQ ID NO: 2.

3. The immunoconjugate of claim 1, wherein the linker moiety is a cysteine residue.

4. The immunoconjugate of claim 3, wherein the cysteine residue is positioned at a terminus of the ghrelin polypeptide.

5. The immunoconjugate of claim 4, wherein the terminus is the carboxy terminus.

6. The immunoconjugate of claim 1, wherein the carrier moiety is KLH or BSA.

7. A composition comprising an immunologically effective amount of the immunoconjugate of claim 1 and a physiologically acceptable vehicle.

8. A method of inducing an anti-ghrelin immune response in a subject comprising administering to the subject the composition of claim 7.

9. A method of controlling adiposity in a subject comprising administering to the subject the composition of claim 7.

* * * * *